United States Patent
Lack et al.

(10) Patent No.: US 10,980,472 B2
(45) Date of Patent: Apr. 20, 2021

(54) METHOD AND APPARATUS FOR SLEEP MONITORING AND CONTROL

(71) Applicant: RE-TIME PTY LTD, Clovelly Park (AU)

(72) Inventors: Leon Lack, Eden Hills (AU); Benjamin Olsen, Austin, TX (US); Vera Townsend, Ovingham (AU); Hannah Scott, Adelaide (AU)

(73) Assignee: Re-Time Pty Ltd., Lonsdale (AU)

( * ) Notice: Subject to any disclaimer, the term of this patent is extended or adjusted under 35 U.S.C. 154(b) by 0 days.

(21) Appl. No.: 16/496,360

(22) PCT Filed: Mar. 20, 2017

(86) PCT No.: PCT/US2017/023240
§ 371 (c)(1),
(2) Date: Sep. 20, 2019

(87) PCT Pub. No.: WO2018/174851
PCT Pub. Date: Sep. 27, 2018

(65) Prior Publication Data
US 2020/0138365 A1 May 7, 2020

(51) Int. Cl.
*A61B 5/00* (2006.01)
*G16H 20/30* (2018.01)
(Continued)

(52) U.S. Cl.
CPC .......... *A61B 5/4809* (2013.01); *A61B 5/1118* (2013.01); *A61B 5/681* (2013.01);
(Continued)

(58) Field of Classification Search
CPC ..... A61B 5/4809; A61B 5/1118; A61B 5/681; A61B 5/6826; A61B 5/7455;
(Continued)

(56) References Cited

U.S. PATENT DOCUMENTS

| 5,259,390 A | 11/1993 | MacLean |
| 6,605,038 B1 | 8/2003 | Teller et al. |

(Continued)

FOREIGN PATENT DOCUMENTS

WO WO2016/035073 3/2016

OTHER PUBLICATIONS

PCT/US17/23240 International Search Report and Written Opinion, dated Jun. 9, 2017.
(Continued)

*Primary Examiner* — Omar Casillashernandez
(74) *Attorney, Agent, or Firm* — Canady & Lortz LLP; Bradley K. Lortz (57) ABSTRACT

A novel apparatus and method is described for sleep monitoring and control by providing tactile stimulation to a user as the user attempts to fall asleep which can be employed for intensive sleep retraining for the treatment of insomnia. A motion response to the tactile stimulation from the user is sensed indicating the user is still awake. The tactile stimulation is periodically repeated and the motion response is evaluated until sleep onset is determined. Following a relatively short set time asleep (e.g. approximately 3 minutes) the user is awakened and the process is reinitiated within a half hour. The technique can be implemented in a small device configuration comparable to a large ring which can be held to a single finger of the user by a band. The single finger both receives the tactile stimulation and provides a motion response and can provide feedback directly to the user.

22 Claims, 8 Drawing Sheets

(51) Int. Cl.
*A61B 5/11* (2006.01)
*A61M 21/00* (2006.01)

(52) U.S. Cl.
CPC .......... *A61B 5/6826* (2013.01); *A61B 5/7455* (2013.01); *A61M 21/00* (2013.01); *G16H 20/30* (2018.01); *A61B 2562/0219* (2013.01); *A61M 2021/0022* (2013.01); *A61M 2205/8206* (2013.01)

(58) Field of Classification Search
CPC .......... A61B 2562/0219; G16H 20/30; A61M 21/00; A61M 2205/8206; A61M 2021/0022
USPC .............................................. 30/575; 340/575
See application file for complete search history.

(56) References Cited

U.S. PATENT DOCUMENTS

| | | | | |
|---|---|---|---|---|
| 8,339,285 | B2* | 12/2012 | Boren | G08B 6/00 340/965 |
| 8,948,861 | B2* | 2/2015 | Rai | A61B 5/4806 340/540 |
| 9,665,169 | B1* | 5/2017 | Dai | G16H 40/67 |
| 2006/0019224 | A1 | 1/2006 | Behar et al. | |
| 2006/0293608 | A1* | 12/2006 | Rothman | A61B 5/4812 600/545 |
| 2010/0318007 | A1* | 12/2010 | O'Brien | A61F 5/56 601/48 |
| 2013/0018284 | A1* | 1/2013 | Kahn | A61B 5/681 600/595 |
| 2014/0370471 | A1* | 12/2014 | Brancaccio | A61B 5/168 434/236 |
| 2015/0038776 | A1* | 2/2015 | Donnet | A61M 21/00 600/28 |
| 2015/0087894 | A1* | 3/2015 | Rink | A61M 21/02 600/28 |
| 2015/0173672 | A1* | 6/2015 | Goldstein | A61B 5/0205 600/301 |
| 2015/0182164 | A1* | 7/2015 | Utter, II | A61B 5/742 600/301 |
| 2015/0273177 | A1* | 10/2015 | Iizuka | A61M 21/02 600/26 |
| 2016/0005291 | A1* | 1/2016 | Takahashi | G04G 13/02 340/575 |
| 2016/0022203 | A1 | 1/2016 | Arnold et al. | |
| 2016/0346501 | A1* | 12/2016 | Hooper | A61B 5/486 |
| 2017/0094046 | A1 | 3/2017 | Raymann et al. | |
| 2017/0360380 | A1* | 12/2017 | Mori | G16H 20/60 |
| 2020/0138365 | A1* | 5/2020 | Lack | A61M 21/00 |

OTHER PUBLICATIONS

Harris et al., "A Randomized Controlled Trial of Intensive Sleep Retraining (ISR): A Brief Conditioning Treatment for Chronic Insomnia," SLEEP 2012;35(1):49-60, 2012.
Harris et al., "Intensive Sleep Retraining treatment for chronic primary insomnia: a preliminary investigation," J. Sleep Res. (2007) 16, 276-284, 2007.

* cited by examiner

METHOD AND APPARATUS FOR SLEEP MONITORING AND CONTROL

BACKGROUND OF THE INVENTION

1. Field of the Invention

This invention relates to methods and apparatuses for sleep retraining. Particularly, this invention relates to methods and apparatuses for sleep retraining employing a user response to tactile stimulation.

2. Description of the Related Art

Chronic insomnia is a sleep disorder that is associated with significant fatigue, irritability, decreased concentration and memory, increased risk of serious accidents and increased healthcare cost. Such consequences can incur significantly impaired quality of life for sufferers and an economic burden to society.

Pharmacotherapy remains a common treatment for chronic insomnia. However, Cognitive Behavioral Therapies (CBT) for insomnia can yield significantly greater benefits than pharmacotherapy and better long-term outcomes. Although benefits gained from pharmacological treatment are immediate, the medication provides symptomatic relief that is not sustained beyond the cessation of treatment. In contrast, the treatment benefits of CBT can remain beyond the termination of treatment.

Stimulus Control Therapy (SCT) is a well known alternative to pharmacotherapy for chronic insomnia. The goals of SCT are to strengthen the bed, bedroom, bedtime activities and the sleep attempt as cues for sleep, and simultaneously to eliminate them as cues for wakefulness by curtailing any sleep-incompatible activities. In general, the requirements for SCT include going to bed only when sleepy, getting out of bed if unable to initiate sleep quickly, arising at the same time each morning, avoiding using the bedroom for activities other than sleep (and sexual activity), and avoiding daytime naps. SCT is the most validated behavioural insomnia treatment with the highest level of supporting empirical evidence and is recommended as a standard treatment by the American Academy of Sleep Medicine.

The theory behind SCT applies an underlying rationale that psychophysiological, or conditioned, insomnia results when the bed and bedroom environment have lost their ability to evoke sleepiness, and become instead a conditioned stimulus for wakefulness. This condition inhibits sleep onset. SCT attempts to reintroduce the sleep environment as a cue for sleepiness. Sleep Restriction Therapy (SRT) similarly uses mild sleep deprivation induced homeostatic sleep pressure to promote improvements in sleep. However, such behavioral treatments typically take between four and eight weekly therapy sessions, and a considerable investment of time and effort may be required for optimum response to these strategies. In addition, the early stages of such therapies may involve truncated sleep, increased sleepiness and fatigue, and resulting problems with patient compliance.

Intensive Sleep Retraining (ISR), is a newer technique for the treatment of chronic insomnia which has been developed. See, A Randomized Controlled Trial of Intensive Sleep Retraining (ISR): A Brief Conditioning Treatment for Chronic Insomnia, by Harris et al., 2012 and Intensive Sleep Retaining Treatment for Chronic Primary Insomnia: a Preliminary Investigation, by Harris et al., 2007. Essentially, ISR involves training a person to fall asleep sooner by experiencing the sensation of falling asleep over and over again. Research participants were repeatedly allowed to fall asleep and after 3-minutes were woken up. This gave participants the sensation of falling asleep, repeatedly, over a short period of time. Falling asleep again and again conditioned participants to fall asleep sooner in the context of the bedroom environment and presumably associated that environment as a cue for falling asleep rather than becoming alert as in the insomnia response.

However, the academic studies providing the foundation for ISR have relied on electroencephalography (EEG) and/or in-laboratory polysomnography (PSG) to determine the moment of sleep onset. These monitoring methods employ expensive and cumbersome equipment that cannot be reasonably utilitized by a home user. In addition, operation of such monitoring equipment requires a technician who must be present during the ISR process to monitor the EEG and detect the moment of sleep onset. In order for ISR to be employed by a home user, an automated, inexpensive, compact, monitoring system which does not require a technician is required.

The Sleep On Cue Application by MicroSleep LLC is an existing smart phone application which implements the ISR principle. The Sleep On Cue App is entirely embodied in a single smart phone running the program (although headphones may be employed for producing the auditory signal). Determination of sleep onset by the Sleep On Cue App is accomplished by periodically generating an auditory tone from the phone. If awake, the user responds to the tone by shaking the phone, which must be held by the user. Sleep onset is determined when the user fails to shake the phone in response to the auditory tone for two consecutive tones. Other methods and apparatuses which may be applicable to monitoring sleep also been developed.

U.S. Pat. No. 5,259,390, issued Nov. 9, 1993, by MacLean describes a vibrating stimulus-response device and method to monitor sleep behaviour. The self-contained portable device can be used in a home environment as a preliminary screen before a more extensive polysomnographic examination.

U.S. Patent Application Publication No. 2006/0019224, published Jan. 26, 2006, by Behar et al. describes a method of automated sleep behavior modification for insomnia and other sleep problems using a computerized treatment system including determining a baseline sleep pattern of a user and storing in the system data indicative of the baseline sleep pattern; generating a sleep behavior regimen based on the stored sleep pattern data and a behavior modification algorithm, wherein the algorithm generates sleep inducement behavior prompts; prompting the user to perform a predetermined sleep inducement behavior at a time determined by the regimen; tracking the sleep behavior of the user and storing data indicative of the tracked sleep behavior; modifying the regimen based on the tracked sleep behavior, and prompting the user to perform the predetermined sleep inducement behavior at a time determined by the modified regimen.

U.S. Patent Application Publication No. 2015/0182164, published Jul. 2, 2015, by Utter, describes a wearable ring (e.g., on a digit of a hand and/or a toe of a foot) may include sensors for generating motion signals in response to a user's body motion, for generating force signals in response to force exerted by a body portion, for generating biometric signals indicative of biometric activity in the body (e.g., heart rate, respiration, arousal), and for generating location signals based on user location. The sensor signals may be processed to monitor parameters that may positively or negatively impact a state of sleep of the user (e.g., time of sleep, quality of sleep, hydration, inflammation, contraction, fatigue, TRHR, accelerometry, arousal of the SNS, etc.). Data derived from the processed signals may be presented (e.g., visually, sound, email, text message, tactile, webpage, etc.) to the user in a format (e.g., reports, notifications, coaching, avoidance, mood) intended to instruct/encourage the user to improve their state of sleep.

U.S. Patent Application Publication No. 2016/0022203, published Jan. 28, 2016, by Arnold et al., describes aspects of automatically detecting periods of sleep of a user of a wearable electronic device. For example, in one aspect, an embodiment may obtain a set of features for periods of time from motion data obtained from a set of one or more motion sensors in the wearable electronic device or data derived therefrom. The wearable electronic device may then classify the periods of time into one of a plurality of statuses of the user based on the set of features determined for the periods of time, where the statuses are indicative of relative degree of movement of the user. The wearable electronic device may also derive blocks of time each covering one or more of the periods of time during which the user is in one of a plurality of states, wherein the states include an awake state and an asleep state.

In view of the foregoing, there is a need in the art for improved techniques for sleep monitoring and control which can be applied to sleep retraining allowing sufferers from sleep disorders to improve their sleep. There is particularly a need for methods and apparatuses to implement ISR for a home user. There is a need for such methods and apparatuses to be affordable and easy to operate. There is further a need for such methods and apparatuses to operate without requiring the user to affirmatively grasp an object during the process and negligibly interfere with the user's comfort while attempting to fall asleep. There is also a need for such methods and apparatuses to be adjustable and programmable to function across a range of different user requirements. These and other needs are met by the present invention as detailed hereafter.

SUMMARY OF THE INVENTION

A novel apparatus and method is described for sleep monitoring and control by providing tactile stimulation to a user as the user attempts to fall asleep which can be employed for intensive sleep retraining. A motion response to the tactile stimulation from the user is sensed indicating the user is still awake. The tactile stimulation is periodically repeated and the motion response is evaluated until sleep onset is determined. Following a relatively short set time asleep (e.g. approximately 3 minutes) the user is awakened and the process is reinitiated either after a short delay (e.g. 1-3 minutes) or longer within a half hour depending on which delay is optimal for improvement of sleep. The technique can be implemented in a small device configuration comparable to a large ring which can be held to a single finger of the user by a band. The single finger both receives the tactile stimulation and provides a motion response and can provide feedback directly to the user. The technique can also be applied to provide a precise "power nap" of optimized sleep duration.

A typical embodiment of the invention comprises a method for monitoring and control, including providing tactile stimulation to a user with a mechanical vibrator as the user attempts to fall asleep, sensing a motion response to the tactile stimulation from the user with a motion sensor, periodically repeating providing the tactile stimulation to the user and evaluating the motion response with a processor coupled to the mechanical vibrator and the sensor until sleep onset is determined by the processor, and waking the user following a set time asleep after establishing the sleep onset with the processor. Sleep onset can be established after the response is not received from the user for two consecutive instances of the tactile stimulation and sleep data comprises time to sleep onset for a given sleep trial. The motion response of the user can comprise movement of a single finger of the user. Typically, waking the user is performed by activating the mechanical vibrator at a high intensity level and the tactile stimulation is performed by activating the mechanical vibrator at a low intensity level. The set time asleep comprises approximately 3 minutes. Although the set time asleep can comprise a power nap period, e.g. approximately 10 minutes. Following the sleep onset and being awakened, a user can begin a next sleep trial immediately but no later than 30 minutes after being awakened in a previous sleep trial. An overall period for the sleep retraining (e.g 5 hours total) can be set by the user.

In further embodiments of the invention, period between the tactile stimulation can comprise a repeating series of 20 seconds, 25 seconds, 30 seconds, 35 seconds, and 40 seconds, in order. The user can be advised to abort the sleep training after the sleep onset has not been achieved for 20 minutes.

In some embodiments of the invention, the mechanical vibrator can be held against a single finger of the user. A band can be used to hold the mechanical vibrator against the single finger of the user. The sensor can comprise an accelerometer for sensing the motion response of the user, e.g. movement of a single finger of the user. The mechanical vibrator and the sensor can be disposed in a common housing held against a single finger of the user and the common housing can include the processor. A battery within the common housing can be used to power the mechanical vibrator, sensor, and processor. A non-transitory memory (also within the common housing) can be used to store an operating program to be run by the processor for controlling the mechanical vibrator and sensor. The non-transitory memory can further store sleep training data of the results of the sleep training such as the time to sleep onset for each sleep trial. The sleep training data can be downloaded to a computing device (e.g. a smart device such as a smart phone) for review and analysis.

Similarly, an apparatus embodiment of the invention can comprise a mechanical vibrator for providing tactile stimulation to a user as the user attempts to fall asleep, a motion sensor for sensing a motion response to the tactile stimulation from the user, and a processor coupled to the mechanical vibrator and the sensor for periodically repeating providing the tactile stimulation to the user and evaluating the motion response until sleep onset is established and waking the user following a set time asleep after the sleep onset is established. This apparatus embodiment of the invention can be further modified consistent with the any other embodiment of the invention described herein.

BRIEF DESCRIPTION OF THE DRAWINGS

Referring now to the drawings in which like reference numbers represent corresponding parts throughout:

FIGS. 7A to 7E show isometric, top, back, side, and bottom view, respectively, the band of the exemplary embodiment of the invention of FIGS. 3A to 3E.

DETAILED DESCRIPTION OF THE PREFERRED EMBODIMENT

1. Overview

As previously mentioned, embodiments of the invention comprise a novel apparatus and method for sleep monitoring and control by providing tactile stimulation to a user as the user attempts to fall asleep which can be employed for intensive sleep retraining. The use of tactile stimulation and a motion response of the user to implement intensive sleep retraining (ISR) affords the user certain benefits. Tactile stimulation may be less jarring to the user than an audible signal. Accordingly, tactile stimulation may improve the overall effectiveness of ISR. Tactile stimulation is innocuous; a user can employ ISR without disturbing a nearby partner.

Another important capability of embodiments of the invention is the isolation of tactile stimulation to a single finger of the user. A single finger is a uniquely sensitive appendage for detecting the wakeful query as part of the ISR process. However, just as ordinary rings may be worn generally without awareness of the wearer, a device can be implemented to apply tactile stimulation to a single finger without discomfort to the user that would otherwise interfere with sleep onset.

The ability to use the same single finger of the user for detecting the wakeful response, e.g. by sensed movement of the finger, is another feature of embodiments of the present invention. Thus, the ISR can be implemented in a small device configuration comparable to a large ring which can be held to the single finger by a band.

It should be noted that although sleep retraining, particularly using ISR, is the primary application of the described method and apparatus for sleep monitoring and control, that application is not exclusive. The described method and apparatus generally provides accurate information regarding the time of sleep onset, the moment the user falls asleep, as well as a technique for gently waking the user. Sleep retraining such as ISR requires this accurate information regarding the time of sleep onset. However, the described method and apparatus can have other applications.

For example, the described method and apparatus for sleep monitoring and control can be applied to enable a "power nap" which can have a direct benefit on a user (whether or not she suffers from insomnia). A "power nap" is an accurately controlled short nap, typically 10 minutes of sleep, which is known to be optimal, such that the user does not sleep too little, rendering no benefit, or too much, leaving the user feeling groggy; a "power nap" is an optimized sleep duration. Accordingly, although the description hereafter may be presented in the context of sleep retraining, those skilled in the art will appreciate that the method and apparatus for sleep monitoring and control described here can be used for any application requiring accurate information regarding the time of sleep onset as well as a technique for gently waking the user.

2. Exemplary Method Using Tactile Stimulation and Motion Response

ISR requires accurate monitoring a user for the moment of sleep onset, the moment the user falls asleep. In order to avoid the need for expensive electroencephalography (EEG) and/or in-laboratory polysomnography (PSG) equipment to directly monitor the user's brain activity, a call-and-response technique can be employed as a sleep onset correlated indicator. At periodic intervals (e.g. 20 to 40 seconds), a user is prompted with a "call stimulus." As described above, embodiments of the present invention employ a "call stimulus" using tactile stimulation such as one or more vibrator low intensity pulses applied to a single finger of the user. If the user is awake, she produces a detected "response," such as movement of the single finger. To be considered a legitimate response to the stimulus, the response must be initiated within a defined time window following the vibration stimulus. This time window can be varied but typically in a range between 200 msec and 1000 msec from the start of the vibratory stimulus. Finger movements outside of this time window will not be considered as responses to the vibratory stimulus.

Suitable "call stimulus" for a particular user can be determined through a calibration algorithm. For example, using a mechanical vibrator for the call stimulus, the appropriate strength and/or duration for the vibration is set for a particular user such that the vibration is sufficient for the user to notice the vibration if she is already awake but insufficient to wake the user if she is already asleep. Separately, a different, higher vibration level is set such that it will wake the user after the user has been asleep for the specified period after sleep onset is determined.

The periodic intervals between call stimuli can be varied. In general, a constant time interval is not favored because a user may anticipate the next stimulus. Such stimulus anticipation can be a particularly negative effect for chronic insomnia sufferers. Accordingly, embodiments of the present invention can employ a period between the tactile stimulation comprising a repeating series of 20 seconds, 25 seconds, 30 seconds, 35 seconds, and 40 seconds, in order. In other words, the periods between separate tactile stimulation are 20, 25, 30, 35, 40, 20, 25, and so on. It is also possible that the period between the tactile stimulation can be randomly varied within a defined range (e.g. 20-40 seconds).

The call stimuli and responses are monitored and evaluated until sleep onset is determined. Typically, sleep onset is established when the user fails to produce a response to two consecutive call stimuli. (However, note that if the user has failed to fall asleep after a specified attempt period (e.g. 20 minutes), the user is advised to abort the sleep attempt and get out of bed.) If sleep onset is achieved, ISR requires waking the user after a relatively short period of sleep in order to reinitiate the process of falling asleep again. Accordingly, after a set time asleep (e.g. 3 minutes), the user is awakened. Each cycle of attempting to fall a sleep, whether successful or not, is termed a "sleep trial."

Previous ISR studies have typically maintained a schedule such that the next sleep trial begins every 30 minutes. However, such regularity is unnecessary. Accordingly, employing an embodiment of the present invention, upon being awakened, the user can opt to immediately begin another sleep trial. If the user does not reinitiate another sleep trial, she will be prompted automatically 5 minutes after being awakened (e.g. by a flashing light and/or vibration). However, the next sleep trial will begin automatically after 30 minutes if the user has not already reinitiated the process.

The overall sleep retraining process duration can be defined by a user. For example, a user can set a process duration of 1 hour or more. The number of sleep trials actually accomplished during the process duration will depend upon how quickly the user falls asleep and then, upon falling asleep and being awakened, how quickly the next sleep trial is reinitiated. After the overall process duration has expired, the user will be allowed to sleep if she is already asleep. However, if the user is awake, the user will be notified (e.g. by vibration and/or flashing light) that the process duration has completed.

Figure 1:
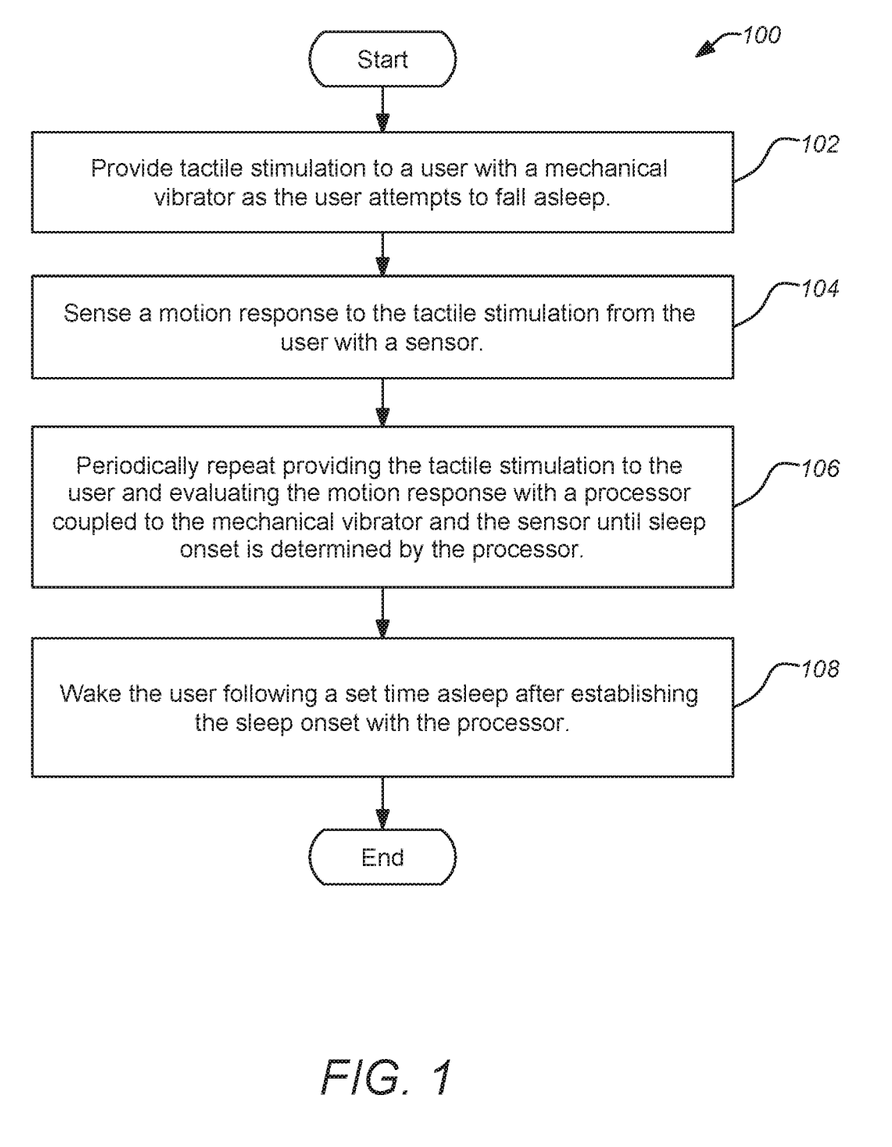
FIG. 1 is a flowchart of an exemplary method for an embodiment of the invention.

FIG. 1 is a flowchart of an exemplary method 100 for an embodiment of the invention. The method 100 for sleep retraining includes a first operation 102 of providing tactile stimulation to a user with a mechanical vibrator as the user attempts to fall asleep. Next, in operation 104, a motion response to the tactile stimulation (within a set time window) from the user is sensed with a sensor. Following this, in operation 106 tactile stimulation to the user is periodically repeated and the motion response from the user, if any, is evaluated with a processor coupled to the mechanical vibrator and the sensor until sleep onset is determined. After establishing the sleep onset, in operation 108, the user is awakened following a set time asleep. This broad method 100 can be modified to comport with any of the detailed requirements described above (e.g. concerning timing between sleep trials, overall sleep retraining duration, etc.). Implementation of the method 100 can be accomplished through programmable device which can be worn on a single finger of the user like a large ring as described hereafter.

3. Exemplary Apparatus Using Tactile Stimulation and Motion Response

Figure 2:
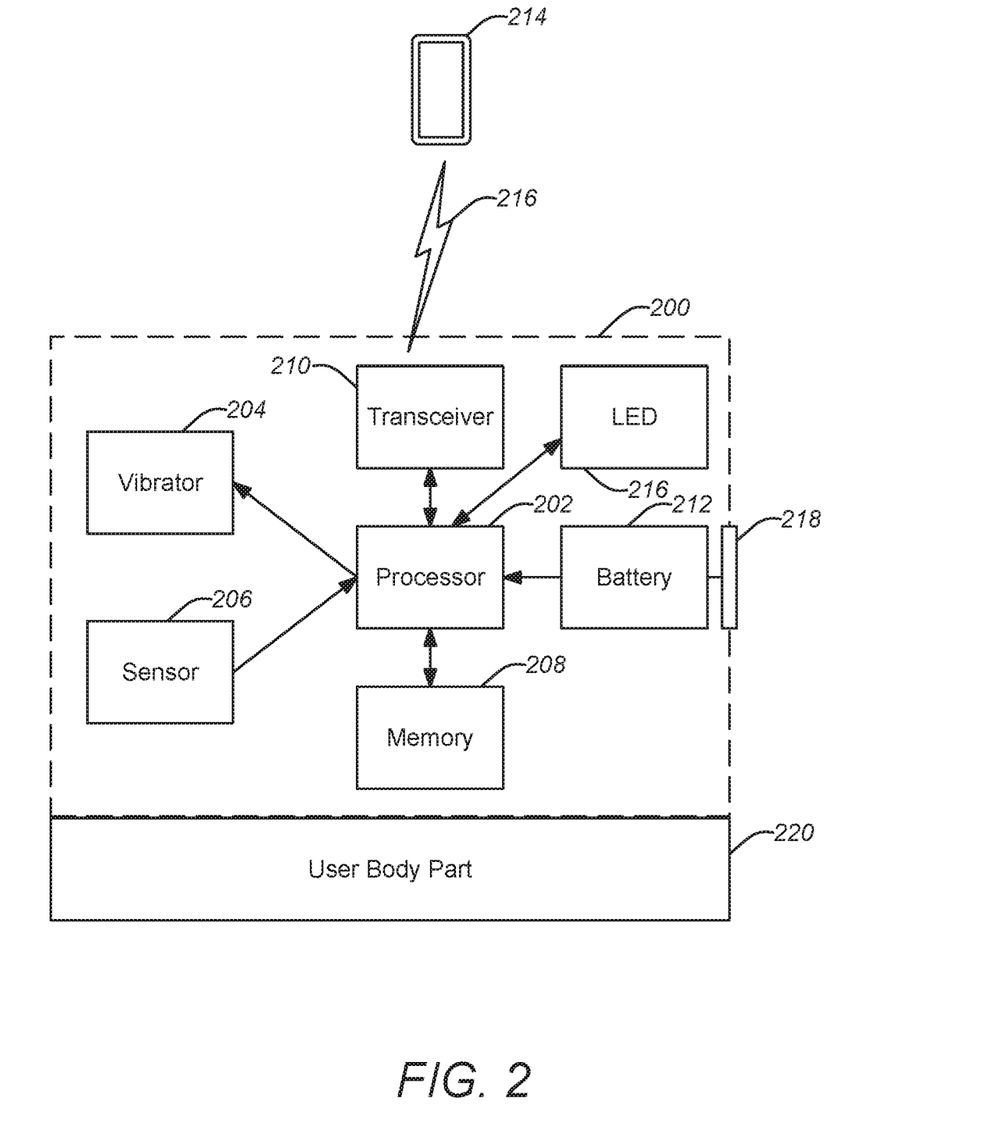
FIG. 2 is a block diagram of an exemplary wearable device comprising an embodiment of the invention.
Figure 3A:
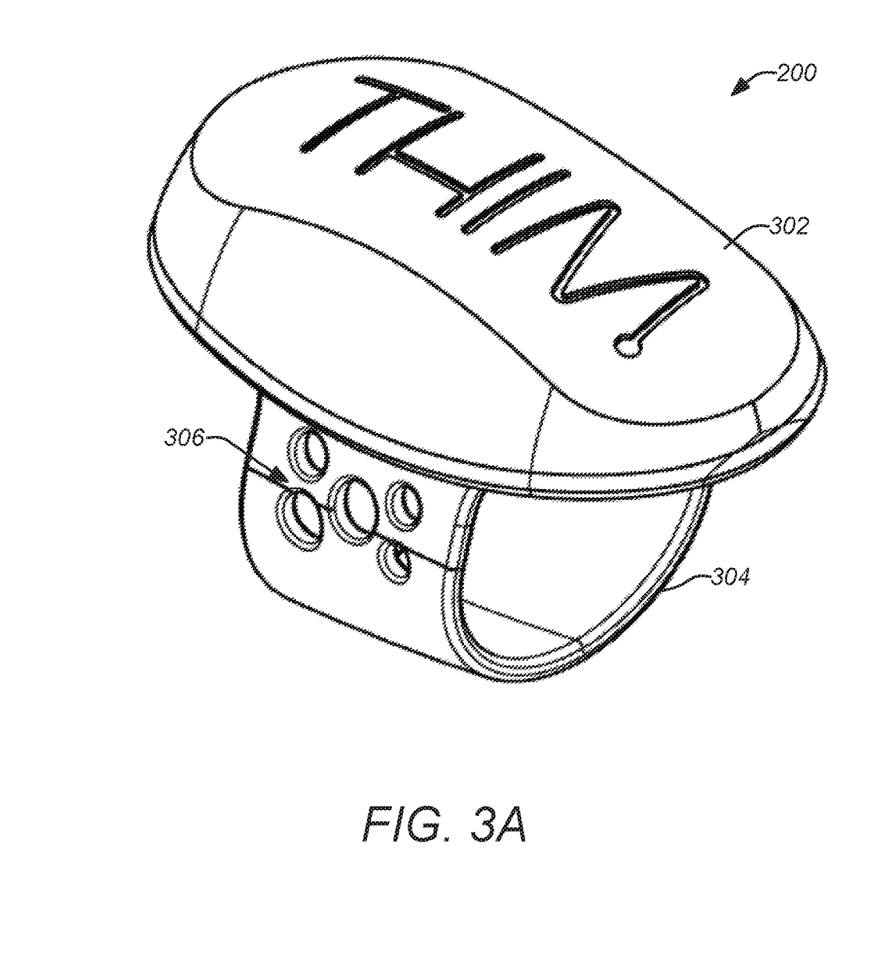
FIGS. 3A to 3E show isometric, top, back, side, and bottom view, respectively, of an exemplary embodiment of the invention for a single finger of a user.
Figure 3B:
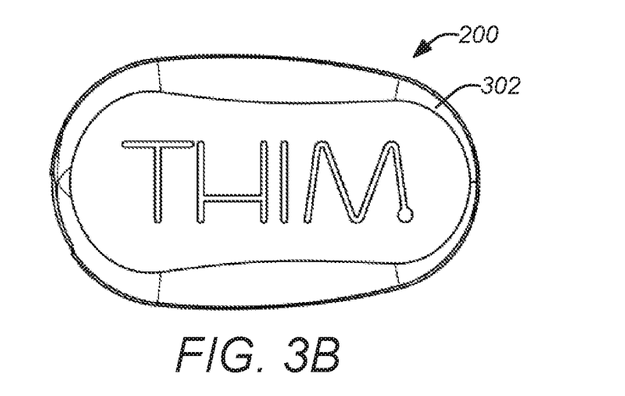
Figure 3C:
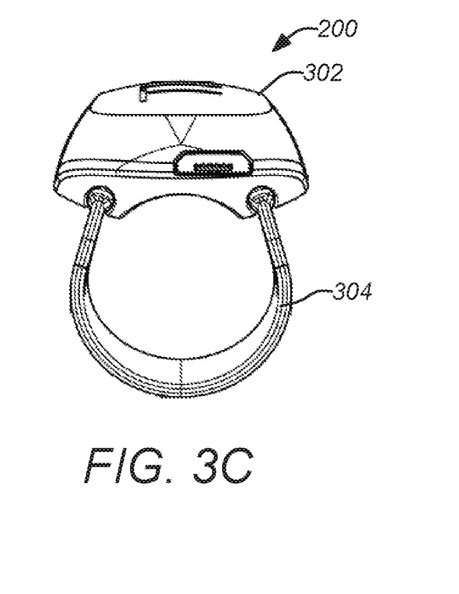
Figure 3D:
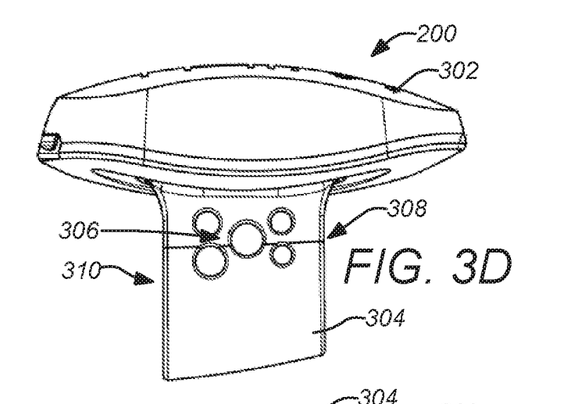
Figure 3E:
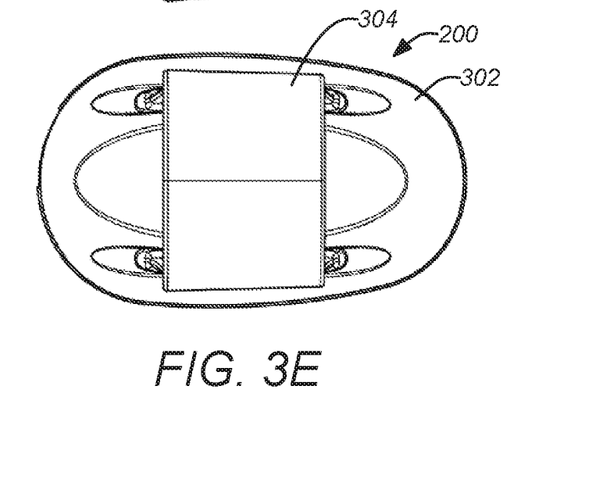

FIG. 2 is a block diagram of an exemplary wearable device 200 comprising an embodiment of the invention. The wearable device 200 is self-contained within a housing enclosing a programmable processor 202 coupled to both a mechanical vibrator 204 (e.g. a coin vibration motor or vibrating disk) and a sensor 206 (e.g. an accelerometer or microgyro). The processor 202 is also coupled to a non-transitory memory 208 (e.g. solid state drive) for storing programming and sleep data and a transceiver 210 for communicating with a remote programmable computing device 214 (e.g. a smart device such as a smart phone) via a wireless protocol 216 (e.g. Bluetooth). A battery 212 (e.g. rechargeable Li ion) provides power to the processor 202 and all other components. The battery 212 can be occasionally recharged through a wired port 218 such as a micro-USB. In addition, the device 200 can also include a light 216 (e.g. a multi-color LED) coupled to the processor 202 in order to provide direct feedback information to the user in the form of color and series of flashes. In use, the device 200 is held against a body part 220 of a user, e.g. a single finger, such that tactile stimulation from the vibrator 204 can be felt by the user and also movement of the body part 220 can be detected by the sensor 206.

The processor 202 is programmed to employ the method 100 described in the previous section through the use of the vibrator 204 and sensor 206. The vibrator 204 is occasionally activated to prompt the user and, if awake, the user responds by moving the device 200 within a set time window (e.g. 200 msec to 1000 msec) to qualify as a response. The sensor 206 detects the motion and the process continues until the user has failed to move the device in response to two consecutive vibration prompts. This pair of consecutive failed responses is interpreted as the moment of sleep onset. The processor 202 is also programmed to keep track of sleep data regarding each completed sleep trial. The timing of all events is tracked and recorded in the memory 208 as sleep data. Sleep data for each sleep trial can include sleep latency, the time from beginning the sleep trial until sleep onset. In addition, the sleep data for each sleep trial is tracked in sequence. Accordingly, changes in sleep latency (ideally improvements) are tracked.

It should be noted that the various functional elements of the exemplary device 200 can be configured in any suitable manner per manufacturing, mechanical and electrical production standards. Accordingly, construction of the device 200 can be formed on a small PCB board providing physical support and electrically coupling the various elements together. Some elements may be provided as a single component (e.g. processor 202 and memory 208). Alternately, some elements may comprise multiple sub-elements (e.g. the transceiver 210 may include electronics and a separate antenna).

The mechanical vibrator 204 has at least two distinct intensity (or power) levels, a low intensity and a high intensity level. The low intensity level of the mechanical vibrator 204 is used as the call stimulus when the user is attempting to fall asleep as previously described. The high intensity level is used to wake the user after being asleep for the prescribed period (e.g. approximately 3 minutes for sleep retraining or approximately 10 minutes for a "power nap"). The tactile sensation between these two intensity levels is sharply apparent to the user (as if they were generated by different devices) so that no confusion ever exists regarding the meaning of a particular stimulus.

Although sleep training is performed autonomously by the wearable device 200, the sleep data can be readily reviewed and analyzed in a specialized application running on a remote programmable computing device 214 such as a smart device or smart phone. In addition, all program settings (e.g. sleep training duration, vibration levels, etc.) can be conveniently adjusted through the smart device application and then transmitted to the device 200 and applied. Accordingly, the transceiver 210 establishes a wireless protocol 216 (e.g. Bluetooth) connection between the programmable computing device 214 and the processor 202 to communicate sleep data and settings. Alternately, wired communication can be used but is not preferred.

The programmable computing device 214, when running the specialized application, synchronizes data and settings with the device 200. The application presents a plurality of interfaces for making all settings related to the sleep control and monitoring. In addition, the application presents the sleep data of the results of each sleep trial, numerically or graphically. For example, the application can show a bar graph of the sleep latency of each consecutive sleep trial for a user to track her progress. A time stamp for each sleep trial is also included in the sleep data.

Another important feature of the device 200 is to provide the user sleep training results information directly, without transmitting sleep data to the programmable computing device 214. This information can be communicated visually through a light (e.g. a multi-color LED) coupled to the processor. Upon completion of a sleep trial after being awakened, the user can be shown a colored light providing an indication of the sleep latency for that sleep trial. For example, a color spectrum range of possible lights including red, orange, yellow, green, blue, indigo, and violet in order can be used such that a colored light at one end of the spectrum (e.g. red) indicates the longest sleep latency and each adjacent color in order indicates a shorter and shorter sleep latency until a colored light at the other end of the spectrum (e.g. violet) indicates the shortest sleep latency. Thus, the user can be provided real time feedback of how long it is taking for her to fall asleep. Ideally, the user should notice sleep latency decreases, indicated by a different color along the spectrum, with each sleep trial and/or with successive nights of undergoing sleep retraining. This is a particularly important feature because it allows the user to get feedback without connecting the device 200 to the programmable computing device 214, which can be turned off. The positive reinforcement of seeing direct improvements in real time reduces anxiety for user which can be crucial to sleep re-training effectiveness.

As previously mentioned, another important feature of the device 200 is the "power nap" mode. In this case, the sleep retraining to improve sleep latency over repeated sleep trials is not performed. Instead, the device 200 applies the described method for monitoring and control of sleep to allow a user to sleep for an accurately controlled power nap period from the time of sleep onset (defined by two failed motion responses by the user as usual). Thus, the device 200 can provide the restorative benefits of a nap while avoiding grogginess experienced when waking from a deep sleep. Typically, the power nap period is 10 minutes. However, embodiments of the invention can employ a nap period set by the user as well.

Although other physical configurations for the device are possible within the scope of the device 200 described above, one exemplary configuration comprises a small compact unit designed to be held against a single finger of the user by a band, like a large ring.

FIGS. 3A to 3E show isometric, top, back, side, and bottom view, respectively, of an exemplary embodiment of the invention for a single finger of a user. The device 200 is enclosed in a contoured housing 302 with a band 304 attached to the bottom forming a ring. When worn, the bottom of the housing 302 is held against the single finger of the user. The user places the ring on a single finger, e.g. index finger, when in use such that the bottom of the housing 302 is held against the single finger. The band 304 is flexible and can be elastic or not. In addition, the band 304 can include perforations 306 which can aid in the elimination of perspiration. Furthermore, the band 304 can be shaped such that the front edge 308 has a smaller circumference than the rear edge 310. This shape helps ensure that the band 304 can be easily put on and taken off by the user.

Figure 4A:
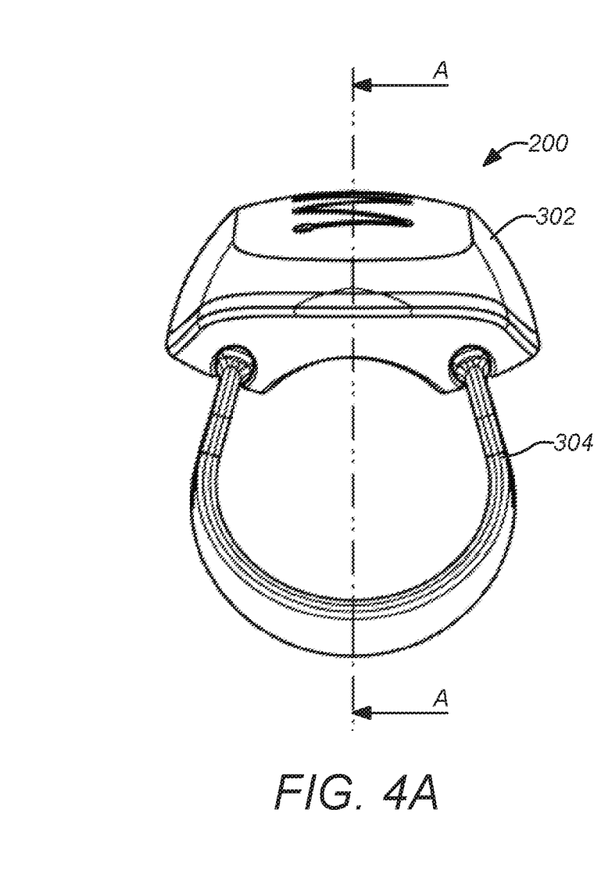
FIGS. 4A and 4B show a cutaway view of the exemplary embodiment of FIGS. 3A to 3E.
Figure 4B:
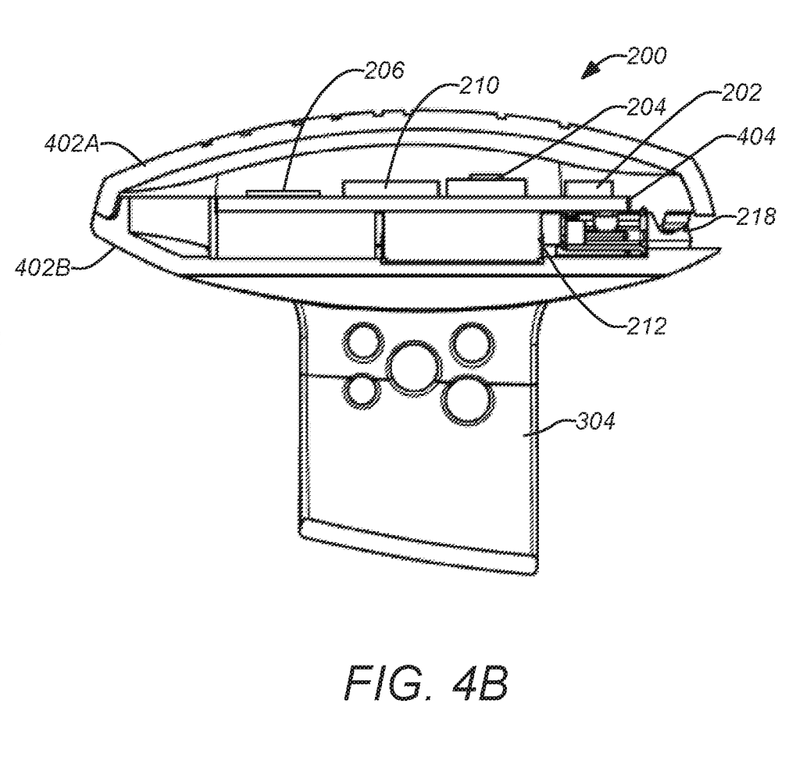
Figure 5A:
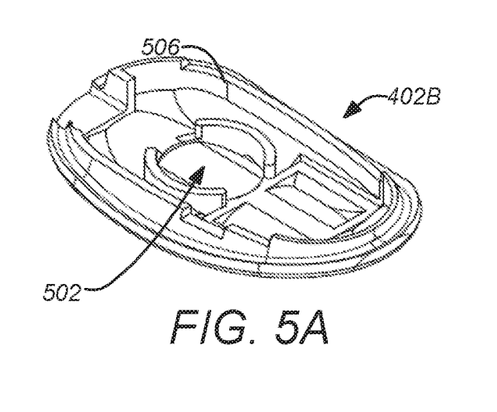
FIGS. 5A to 5E show isometric, top, back, side, and bottom view, respectively, of the lower housing of the exemplary embodiment of the invention of FIGS. 3A to 3E.
Figures 5B, 5D:
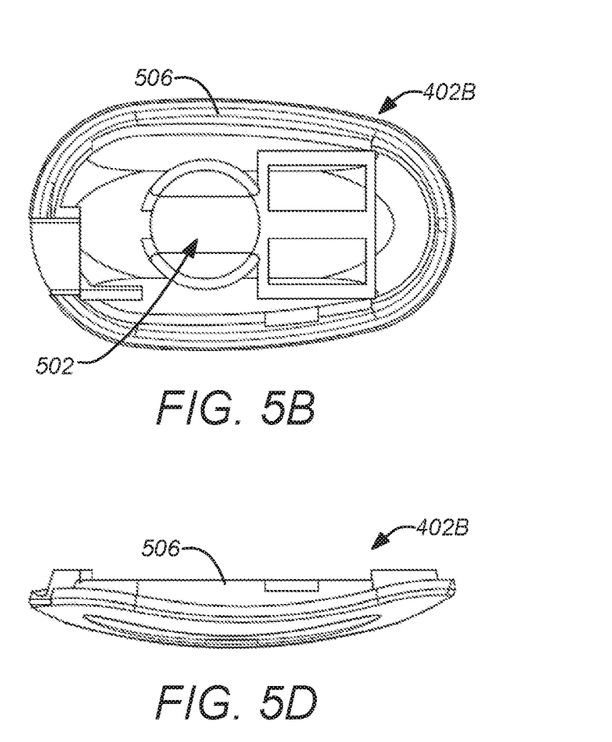
Figure 5C:
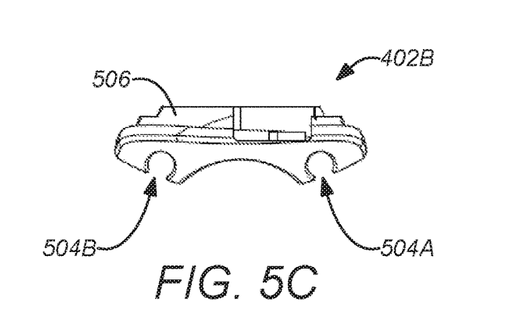
Figure 5E:
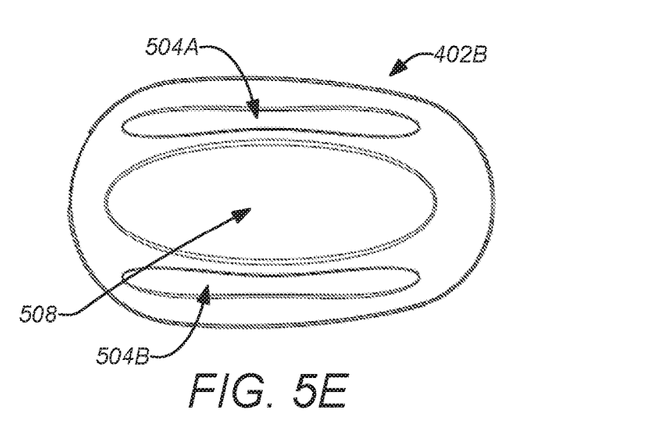
Figure 6A:
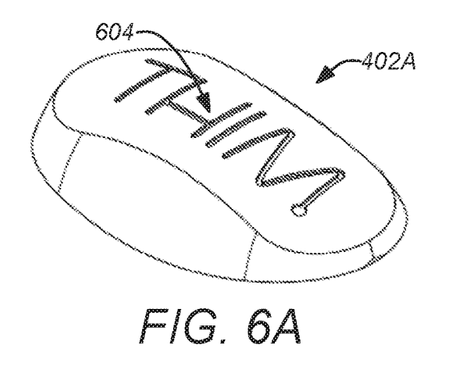
FIGS. 6A to 6E show isometric, top, back, side, and bottom view, respectively, the upper housing of the exemplary embodiment of the invention of FIGS. 3A to 3E.
Figure 6B:
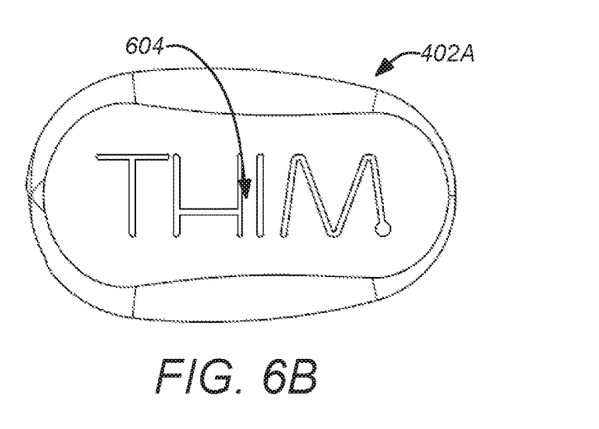
Figure 6C:
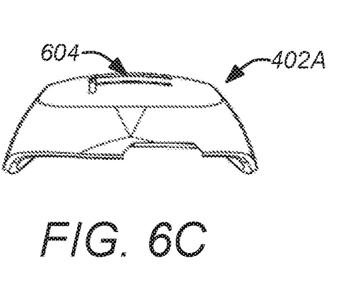
Figure 6D:
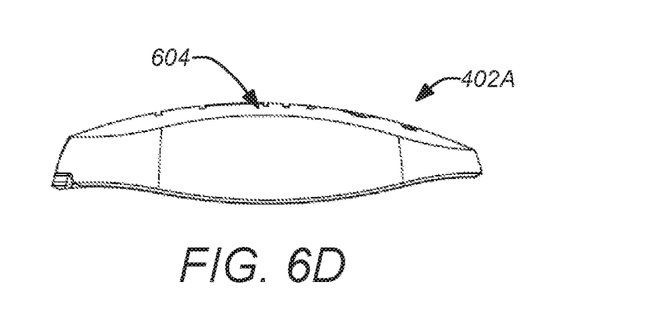
Figure 6E:
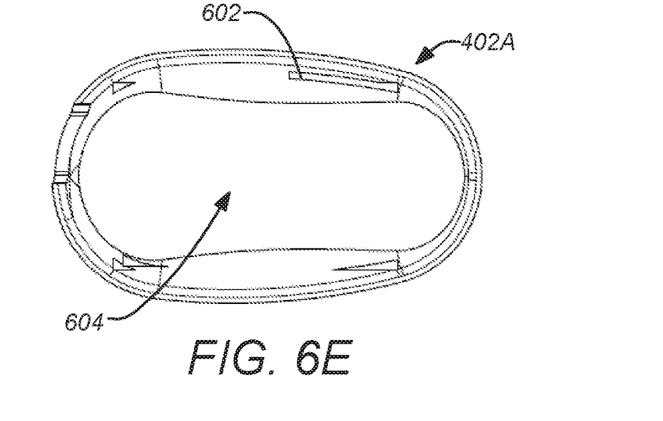
Figure 7B:
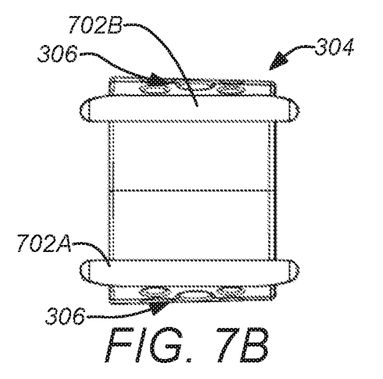
Figure 7C:
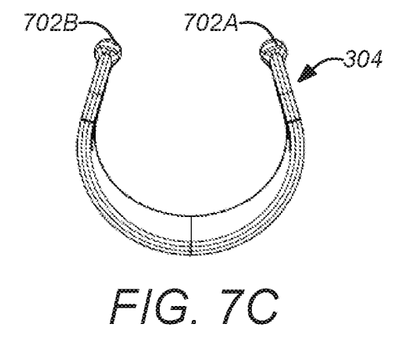
Figure 7D:
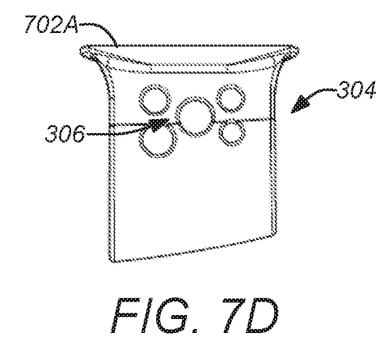
Figure 7E:
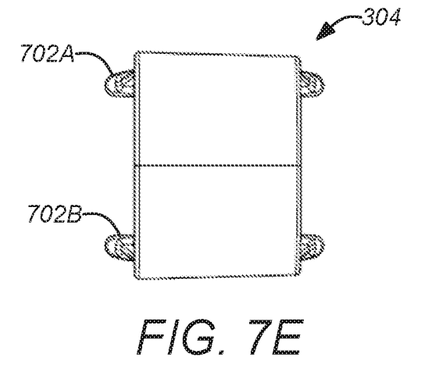

FIGS. 4A and 4B show a cutaway view of the exemplary embodiment of FIGS. 3A to 3E. The housing 302 is shown to be formed from an upper housing 402A and a lower housing 402B which are snap fit together enclosing all the functional elements described in FIG. 2. The port 218 is shown accessible from the rear of the device 200. The various functional elements are generally affixed to a small PCB board 404 which is captured between the upper and lower housings 402A, 402B. Details of the housing and band are shown in the following figures. It should be noted that arrangement of the various components, e.g. processor 202, vibrator 204, motion sensor 206, transceiver 210, and battery 212, are shown as an example only and can be alternately arranged.

FIG. 5A to 5E show isometric, top, back, side, and bottom view, respectively, of the lower housing 402B of the exemplary embodiment of the invention of FIGS. 3A to 3E. The lower housing 402B includes the inner lip 506 around its upper edge which engages a matching outer lip 602 on the upper housing 402A when enclosed around the PCB board 404 of the device 200. The lower housing 402B also includes a recess 502 which can be for the mechanical vibrator 204 in order to place it proximate to the user's finger directly on the opposite side 508 of the lower housing 402B to improve sensitivity or to support the battery 212. If the vibrator 204 is affixed to the PCB board 404, vibration is transmitted directly from the board 404 to the lower housing 402B and the user's finger. In addition, the lower housing also provides lengthwise slots 504A, 504B each having a semicircular hollow cross section which can capture a matching semicircular beading of the band 304 and hold it securely to the lower housing 402B.

FIGS. 6A to 6E show isometric, top, back, side, and bottom view, respectively, the upper housing 402A of the exemplary embodiment of the invention of FIGS. 3A to 3E. The upper housing 402A encloses the PCB board 404 of the device 200 with a snap fit engagement of an outer lip 602 to the matching inner lip 506 of the lower housing 402B. Importantly, the upper housing 402A has a large translucent area 604 so that the light emitted from the LED 216 disposed on the PCB board 404 can be readily observed by the user. Ideally, the upper housing 402A diffuses the light across a wide area of its body to enhance visibility to the user.

FIGS. 7A to 7E show isometric, top, back, side, and bottom view, respectively, the band of the exemplary embodiment of the invention of FIGS. 3A to 3E. As previously mentioned, the band 304 includes perforations 306 which can aid in the elimination of perspiration. In addition, the band 304 is shaped such that the front edge 308 has a smaller circumference than the rear edge 310 to ensure that the band 304 easily put on and removed by the user and worn without any discomfort. The band 304 is attached to the lower housing 402B through beading 702A, 702B at the edge of each end of the band 304 which engages the lengthwise slots 504A, 504B of the lower housing 402B. Each beading 702A, 702B has a semicircular cross section which can engage the matching semicircular hollow slot 504A, 504B of the lower housing 402B.

This concludes the description including the preferred embodiments of the present invention. The foregoing description including the preferred embodiment of the invention has been presented for the purposes of illustration and description. It is not intended to be exhaustive or to limit the invention to the precise forms disclosed. Many modifications and variations are possible within the scope of the foregoing teachings. Additional variations of the present invention may be devised without departing from the inventive concept as set forth in the following claims.

What is claimed is:

1. A method for sleep monitoring and control, comprising:
providing tactile stimulation to a user with a mechanical vibrator as the user attempts to fall asleep, the tactile stimulation being sufficient for the user to notice if the user is already awake but insufficient to wake the user if the user is already asleep;
sensing a wakeful motion response to the tactile stimulation from the user if awake with a motion sensor; and
periodically repeating providing the tactile stimulation to the user and evaluating the wakeful motion response with a processor coupled to the mechanical vibrator and the sensor until sleep onset is determined by the processor;
wherein the sleep onset is established after the response is not received from the user for two consecutive instances of the tactile stimulation and sleep data comprises time to the sleep onset for a given sleep trial.

2. An apparatus for sleep monitoring and control, comprising:
- a mechanical vibrator for providing tactile stimulation to a user as the user attempts to fall asleep, the tactile stimulation being sufficient for the user to notice if the user is already awake but insufficient to wake the user if the user is already asleep;
- a motion sensor for sensing a wakeful motion response to the tactile stimulation from the user if awake; and
- a processor coupled to the mechanical vibrator and the sensor for periodically repeating providing the tactile stimulation to the user and evaluating the wakeful motion response until sleep onset is established;
- wherein the sleep onset is established after the response is not received from the user for two consecutive instances of the tactile stimulation and sleep data comprises time to the sleep onset for a given sleep trial.

3. The method of claim 1, further comprising waking the user following a set time asleep after establishing the sleep onset with the processor.

4. The method of claim 3, wherein waking the user is performed by activating the mechanical vibrator at a high intensity level and the tactile stimulation is performed by activating the mechanical vibrator at a low intensity level.

5. The method of claim 3, wherein the set time asleep comprises 3 minutes.

6. The method of claim 1, wherein a period between the tactile stimulation comprises an increasing series in order.

7. The method of claim 3, wherein following the sleep onset and being awakened, a user can begin a next sleep trial immediately but no later than 30 minutes after being awakened in a previous sleep trial.

8. The method of claim 1, wherein the user is advised to abort the method for sleep monitoring and control after the sleep onset has not been achieved for 20 minutes.

9. The method of claim 1, wherein the mechanical vibrator is held against a single finger of the user.

10. The method of claim 1, wherein the motion response of the user comprises movement of a single finger of the user.

11. The apparatus of claim 2, wherein the sensor comprises an accelerometer for sensing the movement of a single finger of the user.

12. The apparatus of claim 2, wherein the processor, the mechanical vibrator and the sensor are disposed in a common housing.

13. The apparatus of claim 2, wherein a non-transitory memory stores an operating program to be run by the processor for controlling the mechanical vibrator and sensor.

14. The apparatus of claim 13, wherein the non-transitory memory further stores sleep training data of results of sleep training performed by the apparatus for sleep monitoring and control.

15. The apparatus of claim 14, wherein the sleep training data comprises time to sleep onset for each sleep trial.

16. The apparatus of claim 14, wherein the sleep training data is downloaded to a computing device for review and analysis.

17. The method of claim 1, wherein an overall period for the sleep retraining is set by the user.

18. The method of claim 1, wherein a period between the tactile stimulation is randomly varied.

19. The apparatus of claim 2, wherein a period between the tactile stimulation is randomly varied.

20. The method of claim 1, wherein the set time asleep comprises a power nap period such that the user does not sleep to render no benefit or to leave the user feeling groggy.

21. The apparatus of claim 2, wherein the set time asleep comprises a power nap period such that the user does not sleep to render no benefit or to leave the user feeling groggy.

22. The apparatus of claim 2, further comprising waking the user following a set time asleep after establishing the sleep onset with the processor.

* * * * *